(12) United States Patent
Timm (10) Patent No.: US 8,221,824 B2
(45) Date of Patent: *Jul. 17, 2012

(54) DEFORMING SURFACE OF DRUG ELUTING COATING TO ALTER DRUG RELEASE PROFILE OF A MEDICAL DEVICE

(75) Inventor: Mary Jo Timm, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2196 days.

This patent is subject to a terminal disclaimer.

(21) Appl. No.: 11/050,217

(22) Filed: Feb. 3, 2005

(65) Prior Publication Data

US 2006/0171982 A1 Aug. 3, 2006

(51) Int. Cl.
*B05D 3/10* (2006.01)
*B05D 3/12* (2006.01)

(52) U.S. Cl. .................................. 427/2.25
(58) Field of Classification Search .............. 427/2.25
See application file for complete search history.

(56) References Cited

U.S. PATENT DOCUMENTS

| | | | |
|---|---|---|---|
| 4,601,893 A * | 7/1986 | Cardinal | 424/424 |
| 5,091,205 A | 2/1992 | Fan | |
| 5,797,887 A | 8/1998 | Rosen et al. | |
| 6,063,102 A * | 5/2000 | Morales | 606/198 |
| 6,190,404 B1 | 2/2001 | Palmaz et al. | |
| 6,274,294 B1 | 8/2001 | Hines | |
| 6,280,411 B1 | 8/2001 | Lennox | |
| 6,368,658 B1 * | 4/2002 | Schwarz et al. | 427/2.15 |
| 6,451,373 B1 | 9/2002 | Hossainy et al. | |
| 6,506,437 B1 | 1/2003 | Harish et al. | |
| 6,558,422 B1 | 5/2003 | Baker et al. | |
| 6,558,733 B1 | 5/2003 | Hossainy et al. | |
| 6,562,065 B1 | 5/2003 | Shanley | |
| 6,629,350 B2 * | 10/2003 | Motsenbocker | 29/283.5 |
| 6,756,007 B2 | 6/2004 | Pletzer et al. | |
| 6,805,898 B1 | 10/2004 | Wu et al. | |
| 6,815,609 B1 | 11/2004 | Wang et al. | |
| 6,846,985 B2 | 1/2005 | Wang et al. | |
| 6,904,658 B2 | 6/2005 | Hines | |
| 6,908,622 B2 | 6/2005 | Barry et al. | |
| 6,914,412 B2 | 7/2005 | Wang et al. | |
| 7,049,348 B2 | 5/2006 | Evans et al. | |
| 7,090,888 B2 | 8/2006 | Snyder et al. | |
| 7,091,412 B2 | 8/2006 | Wang et al. | |
| 7,162,302 B2 | 1/2007 | Wang et al. | |
| 7,220,275 B2 | 5/2007 | Davidson et al. | |
| 7,220,755 B2 | 5/2007 | Betts et al. | |
| 7,291,165 B2 | 11/2007 | Rosenthal et al. | |
| 7,479,128 B1 | 1/2009 | Lenz | |
| 7,935,379 B2 * | 5/2011 | Radhakrishnan et al. | 427/2.1 |
| 2001/0047203 A1 | 11/2001 | Dalton | |
| 2002/0050220 A1 | 5/2002 | Schueller et al. | |
| 2003/0031780 A1 * | 2/2003 | Chudzik et al. | 427/2.1 |
| 2003/0149479 A1 | 8/2003 | Snyder et al. | |
| 2003/0233141 A1 | 12/2003 | Israel | |
| 2004/0164291 A1 | 8/2004 | Wang et al. | |
| 2004/0210289 A1 | 10/2004 | Wang et al. | |
| 2004/0254419 A1 | 12/2004 | Wang et al. | |
| 2004/0258914 A1 * | 12/2004 | Chandra et al. | 428/375 |
| 2005/0025797 A1 | 2/2005 | Wang et al. | |
| 2005/0079132 A1 | 4/2005 | Wang et al. | |
| 2005/0090888 A1 | 4/2005 | Hines et al. | |
| 2005/0107870 A1 | 5/2005 | Wang et al. | |
| 2005/0135759 A1 | 6/2005 | Wang et al. | |
| 2006/0025848 A1 | 2/2006 | Weber et al. | |
| 2006/0034884 A1 | 2/2006 | Stenzel | |
| 2007/0112421 A1 | 5/2007 | O'Brien | |

FOREIGN PATENT DOCUMENTS

| | | |
|---|---|---|
| GB | 1 336 699 A | 11/1973 |
| WO | 03/037223 A1 | 5/2003 |
| WO | 2004/043509 A1 | 5/2004 |
| WO | 2005/091834 A2 | 10/2005 |
| WO | WO 2006/020660 A | 2/2006 |

OTHER PUBLICATIONS thefreedictionary.com [online] Retrieved on Mar. 29, 2009 from the Internet: <URL: http://www.thefreedictionary.com/impact.*
thefreedictionary.com ([Retrieved online on Oct. 24, 2009]. Retrieved from the Internet: URL: http//www.thefreedictionary.com/clamp).*
Neervannan, Seshadri, et al., "Dependence of Dissolution Rate on Surface Area: Is a Simple Linear Relationship Valid for Co-Compressed Drug Mixtures?" Pharmaceutical Research, vol. 11, No. 10, pp. 1391-1395 (1994).
Xia, Younan, et al., "Soft Lithography," Annual Review of Materials Science, vol. 28, pp. 153-184 (1998).

* cited by examiner

*Primary Examiner* — Jeffrey S. Lundgren
*Assistant Examiner* — Nelson Blakely, III
(74) *Attorney, Agent, or Firm* — Kenyon & Kenyon LLP (57) ABSTRACT

A method is provided for altering a drug release profile of a coating of a medical device by increasing a surface area of the coating of the medical device. The method may include indenting the coating using a crimping apparatus, a rolling apparatus, or a clamping device. The method may alternatively or additionally include changing a chemical composition of at least one coating component to increase a roughness of a texture of the coating, and/or drying or partially drying the coating before the coating impacts the medical device.

20 Claims, 7 Drawing Sheets

DEFORMING SURFACE OF DRUG ELUTING COATING TO ALTER DRUG RELEASE PROFILE OF A MEDICAL DEVICE

FIELD OF THE INVENTION

The present invention relates to the manufacturing of medical appliances. More particularly, the present invention relates to a method and device for deforming a coating on a medical appliance to alter a drug release profile.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

The type, thickness and other properties of the polymer and/or therapeutic agent may be chosen to create different release kinetics. Coatings may be applied to medical devices by processes such as dipping, spraying, vapor deposition, plasma polymerization, and electrodeposition. Although these processes may be used to produce satisfactory coatings, they are all subject to a drawback. After the coating process, stents may need to endure further handling as part of the manufacturing process. For instance, stents may need to be crimped onto a balloon. This further handling may cause deformities in the coating. Additionally, the drying process, or even the coating process itself, may lead to uneven coating and/or an uneven coating surface. An uneven coating surface may lead to a less predictable Kinetic Drug Release (KDR), which may lead to an individual stent or a batch of stents (or other medical devices) failing quality control. A non-uniform or uneven coating may lead to the unit failing KDR, drug uniformity and coating thickness specifications.

Therefore, an uneven coating surface has traditionally been an unwanted, though often inevitable, result of the manufacturing process. There is, therefore, a need for a cost-effective method of coating devices that results in uniform, defect-free coatings and uniform drug doses per unit device. The method would allow for better control of the sensitivity of the bioactive material and would also reduce variations in the coating properties between medical devices.

To alter the KDR profile of a Drug Eluting (DE) product, typically either the formulation of the drug/carrier or application of an overcoat is required. Each of these methods involves altering the chemistry and potentially impacting the efficacy/bio-compatibility of the product.

SUMMARY

A method is provided for altering a drug release profile of a coating of a medical device. The method includes: determining the drug release profile of the coating of the medical device; determining an increased surface area necessary to alter the drug release profile to an altered drug release profile; and increasing a surface area of the coating of the medical device to obtain the altered drug release profile.

The method may further include determining a surface area of the coating of the medical device. In the method, the increasing of the surface area of the coating of the medical device may include indenting the coating. In the method, the indenting of the coating may include pressing the medical device, rolling the medical device, and/or crimping the medical device. In the method, the indenting of the coating may include creating angular indentations, rounded dimples, curved impressions, and/or linear edges.

In the method, a size of an indentation of the coating may be increased. In the method, a depth of an indentation of the coating may be increased. In the method, a spacing between indentations of the coating may be decreased. In the method, the indenting of the coating may include creating random indentations and/or regularly patterned indentations.

A method is provided for improving a drug release profile of a coating of a medical device. The method includes: determining an expected drug release profile of the coating of the medical device using first process parameters of a coating method; determining an increased surface area necessary to obtain an improved drug release profile; and altering the first process parameters to second process parameters of the coating method to achieve the increased surface area. Additionally, deforming the surface may ameliorate any changes to the drug release profile due to handling of the part during post-coating. The surface of the part may be made consistently inconsistent such that changes occurring during manipulations post-coating do not effect the drug release profile.

In the method, the altering of the first process parameters to the second process parameters may further include changing a chemical composition of at least one coating component to increase a roughness of a texture of the coating. In the method, the altering of the first process parameters to the second process parameters may include drying the coating before the coating impacts the medical device.

In the method, the coating method may include a suspended air coating method and the altering of the first process parameters to the second process parameters may include increasing a number of further medical devices coated simultaneously with the medical device, increasing a force of air suspending the medical device, and/or increasing a time of suspending the medical device.

A device is provided for altering a drug release profile of a coating of a medical device. The device includes an arrangement adapted to hold the medical device and an arrangement adapted to indent a surface area of the coating.

In the device, the arrangement adapted to indent the surface of the coating may include a rolling apparatus.

In the device, the arrangement adapted to indent the surface of the coating may include a pressing apparatus.

In the device, the arrangement adapted to indent the surface of the coating may include a crimping apparatus. In the device, the arrangement adapted to indent the surface of the coating includes dimples. In the device, the dimples are arranged in a regular pattern on the arrangement adapted to indent the surface of the coating.

In the device, the arrangement adapted to hold the medical device includes a mandrel.

DETAILED DESCRIPTION

As medical devices and/or stents move toward thinner struts and/or reduced surface areas, controlling KDR through surface area changes may be valuable. Additionally, KDR for finished parts may be different from that of component parts due to disruption of the coating during handling. If the surface is dimpled prior to or subsequent to handling, the effects of handling may be reduced or eliminated.

According to an exemplary embodiment of the present invention, a method is provided for physically altering or deforming the surface of the drug eluting coating in a consistent manner to increase surface area and increase KDR to a desired level. This may be achieved by: post-processing (e.g., using a mechanical device to dimple the surface); choice of coating method (e.g., selecting a method that can consistently make the surface textured); and altering processing parameters to obtain a surface texture (e.g., applying parameters that result in a variable surface texture).

Each of these techniques may cause the surface area of the coating to be increased within a given range of variation.

Various improvements over conventional methods are possible using an exemplary method of the present invention. With post-processing, the same coated part may be altered in different ways to produce several different KDR profiles. Chemical components may remain unaltered while the surface area and KDR are altered. Subtle changes in KDR may be achieved readily through formulation/barrier layers.

Figure 1:
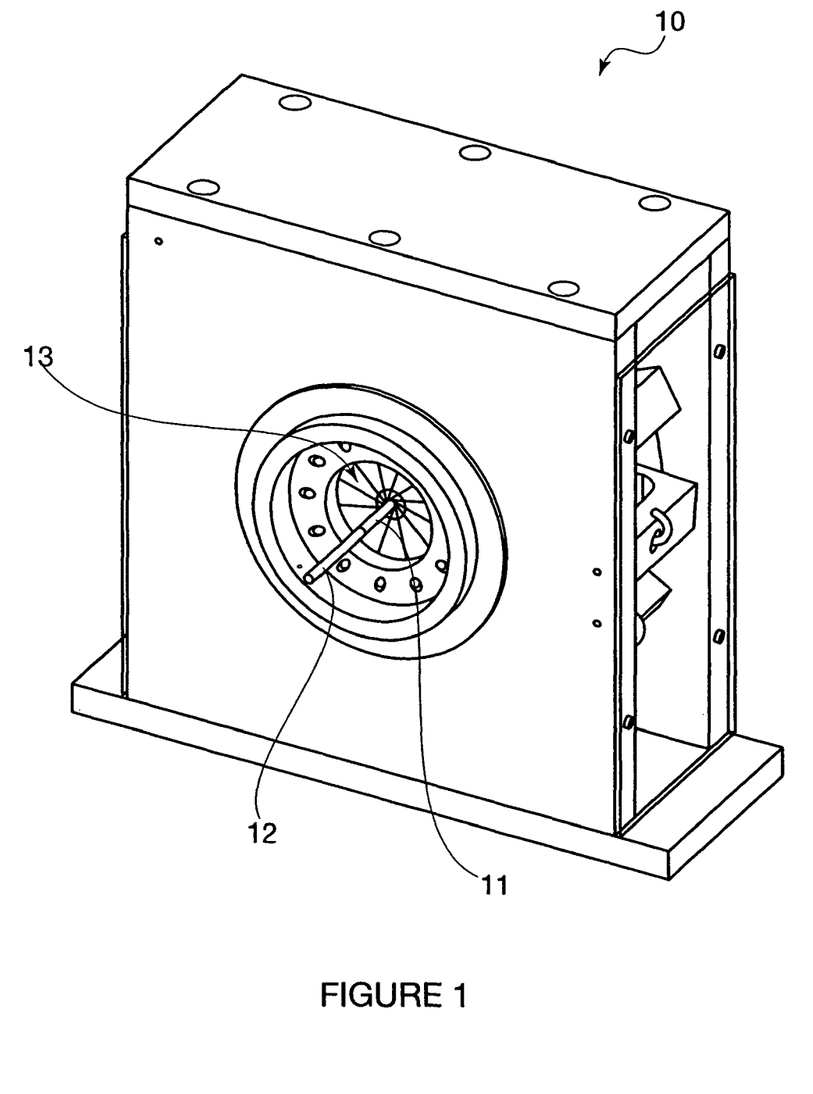
FIG. 1 illustrates an exemplary embodiment of a crimping device used to perform an exemplary method of the present invention with a stent being crimped.

FIG. 1 illustrates an exemplary embodiment of crimping device 10 performing a crimp on stent 11. Stent 11 is held in mandrel 12 and is inserted into crimping device 10. Stent 11 is arranged in constricting zone 13 of crimping device 10. Crimping device 10 may then be operated to constrict around stent 11, thereby crimping stent 11. A pattern of projections on crimping device 10 may thereby be pressed into the surface of the coating of stent 11. The indentations caused by the projections on crimping device 10 may increase the surface area of the coating of stent 11, and may thereby increase the KDR profile of stent 11.

Figure 2:
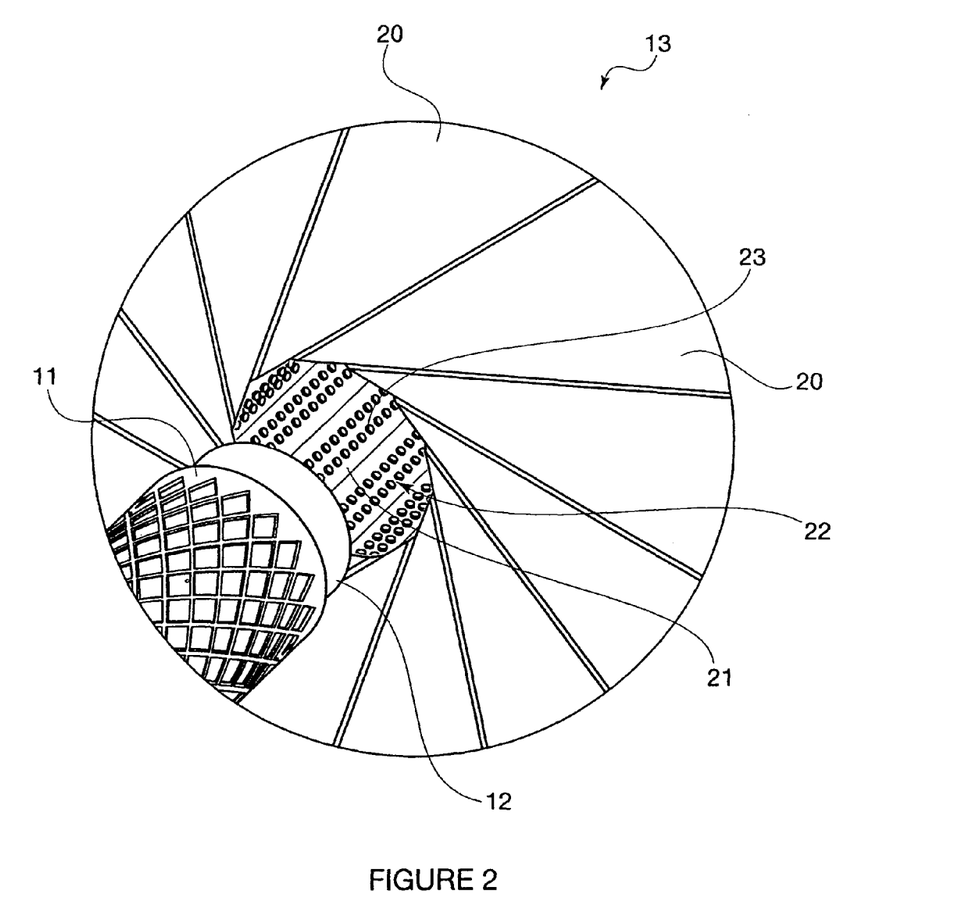
FIG. 2 illustrates a close-up view of the crimping device shown in FIG. 1 with a stent being crimped.

FIG. 2 illustrates a close-up view of crimping device 10 shown in FIG. 1 with stent 11 being held on mandrel 12 and being crimped. Iris elements 20 operate together to form constricting zone 13. Each iris element 20 has a face 21 arranged towards an interior space which is adapted to accept stent 11 on mandrel 12. Each face 21 of iris element 20 has pattern 22 arranged to provide relief and to create indentations on the surface of the coating of stent 11 when stent 11 is placed in crimping device 10 and iris elements 20 are moved radially inward. Pattern 22 in the exemplary embodiment shown in FIG. 2 is composed of regularly arranged dimples 23. Alternatively, any other shape may be used instead of or in addition to dimple 23. Also, dimples 23 (or any other appropriate shape) may be arranged in a random or pseudo-random pattern on face 21.

The operation of crimping device 10 may be part of the manufacturing process of stent 11. In particular, crimping device 10 may be used to crimp stent 11 onto a balloon catheter or similar medical device. This crimping may induce a temporary or permanent deformation of stent 11 to secure stent 11 to the balloon.

Figure 3:
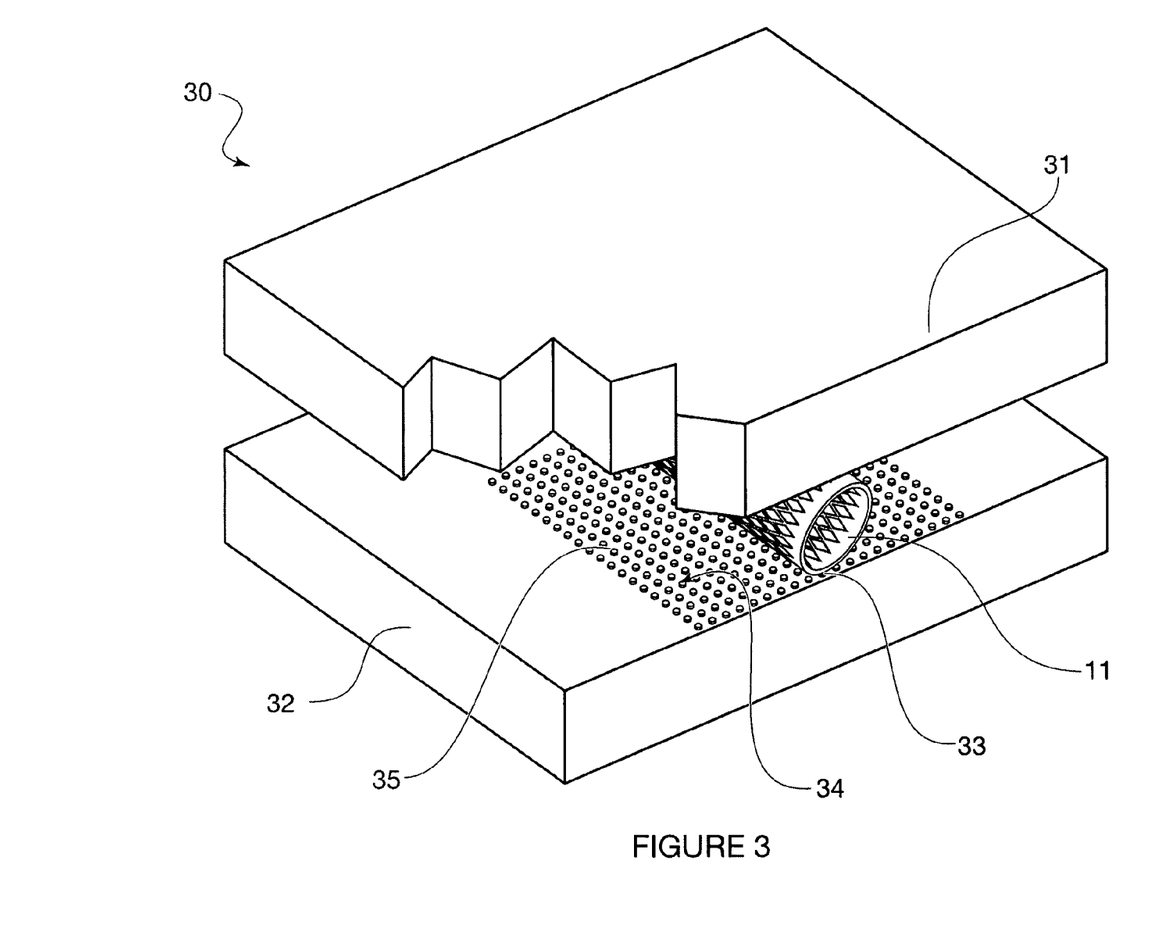
FIG. 3 illustrates an exemplary embodiment of a rolling device used to perform an exemplary method of the present invention with a stent being rolled.

FIG. 3 illustrates an exemplary embodiment of rolling device 30 used to perform an exemplary method of the present invention with stent 11 being rolled. Rolling device 30 includes upper plate 31 and lower plate 32, though the plates may be interchangeable and may alternatively be oriented side by side or possibly in another configuration. Lower plate 32 includes pattern area 34 which includes dimples 35 arranged in a uniform pattern. Alternatively, pattern area 34 may include raised or indented elements in any other pattern, which may be uniform, random, or pseudo-random. Additionally, upper plate 31 may include a pattern area that may match pattern area 34 of lower plate 32 or may be a different pattern. Stent 11 may contact lower plate 32 at contact zone 33 that may cause dimples 35 of pattern area 34 to contact the coating of stent 11. Dimples 35 may create indentations in the coating of stent 11 and may therefore increase the surface area of the coating of stent 11, thereby altering (possibly increasing) the KDR profile of the drug in the coating of stent 11.

Rolling device 30 may be operated by placing stent 11 on lower plate 32 and then bringing upper plate 31 into proximity with lower plate 32 so that upper plate 31 contacts stent 11. Stent 11 may be placed in rolling device 30 before or after being crimped onto a balloon. By sandwiching stent 11 between lower plate 32 and upper plate 31, stent 11 may be held securely in place. Lower plate 32 and upper plate 31 may be brought close enough to each other to hold stent 11 without deformation, with some deformation but without permanent deformation, or with permanent deformation. Lower plate 32 may be moved laterally with respect to upper plate 31 to cause stent 11 to roll between the plates. Alternatively upper plate 31 may be moved with respect to lower plate 32, or both plates may be moved laterally and simultaneously in opposite directions. After contacting some or all of the surface of stent 11 with dimples 35 of pattern area 34, the plates may be separated and stent 11 may be removed from between upper plate 31 and lower plate 32.

Figure 4:
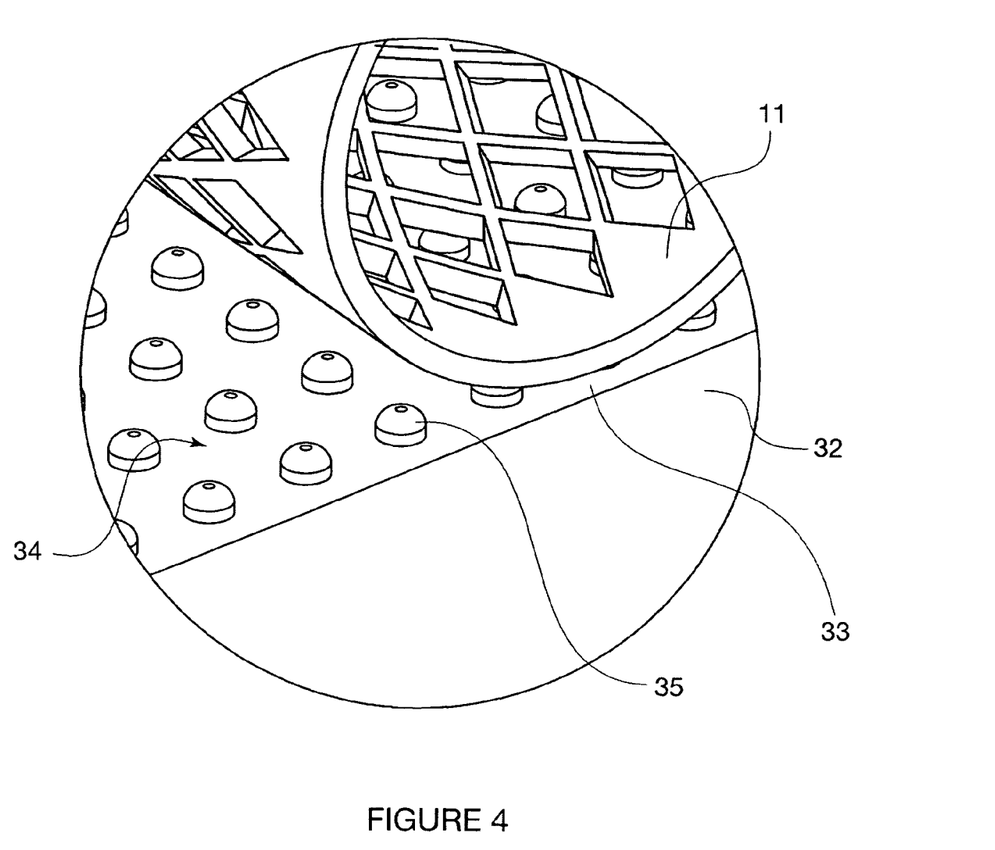
FIG. 4 illustrates a close-up view of the rolling device shown in FIG. 3 with a stent being rolled.

FIG. 4 illustrates a close-up view of rolling device 30 shown in FIG. 3 with stent 11 being rolled. Lower plate 32 is shown having pattern area 34 including dimples 35. Stent 11 contacts lower plate 32 at contact zone 33, thereby causing dimples 35 to contact the coating of stent 11 and to cause indentations in the surface of the coating of stent 11.

Figure 5:
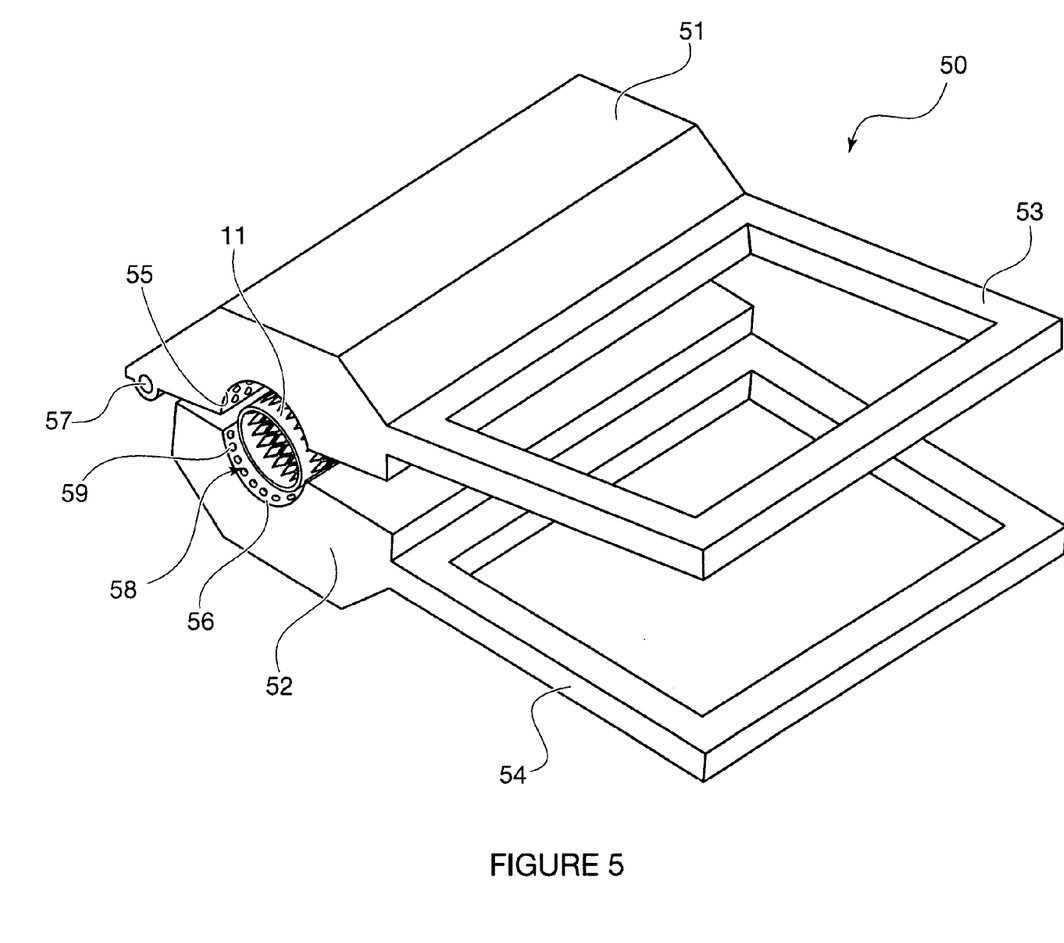
FIG. 5 illustrates an exemplary embodiment of a clamping device used to perform an exemplary method of the present invention with a stent being clamped.

FIG. 5 illustrates an exemplary embodiment of clamping device 50 used to perform an exemplary method of the present invention with stent 11 being clamped. Clamping device 50 includes upper clamp section 51 and lower clamp section 52, which may be connected by hinge 57. Upper clamp section 51 includes upper handle 53 and lower clamp section 52 includes lower handle 54. Upper handle 53 and lower handle 54 may be operated manually or mechanically to move upper clamp section 51 and lower clamp section 52 towards and away from each other about the line defined by hinge 57. Upper clamp section 51 may have upper clamping surface 55 and lower clamp section 52 may have lower clamping surface 56. Upper clamping surface 55 and lower clamping surface 56 may be designed to accommodate stent 11 between their opposing surfaces with no force exerted on stent 11, with some force exerted on stent 11 but not enough force to deform stent 11, or with enough force to deform (either temporarily or permanently) stent 11. Upper clamping surface 55 and/or lower clamping surface 56 may have pattern region 58 arranged thereon on all or part of their opposing surfaces. Pattern region 58 may include dimples 59 arranged in a uniform pattern, or may include other raised elements and/or depressions, in any other type of pattern.

Clamping device 50 may be operated by placing stent 11 (which may have been coated with a drug-eluting compound) between upper clamping surface 55 and lower clamping surface 56 while clamping device 50 is in an open configuration (i.e., upper clamp section 51 and lower clamp section 52 are separated). After inserting stent 11, upper handle 53 and lower handle 54 may be operated manually or mechanically to move upper clamp section 51 and lower clamp section 52 towards each other, causing dimples 59 to indent the coating of stent 11. Thereafter, upper handle 53 and lower handle 54 may be operated manually or mechanically to move upper clamp section 51 and lower clamp section 52 away from each other. Stent 11 may thereafter be removed from clamping device 50.

Figure 6:
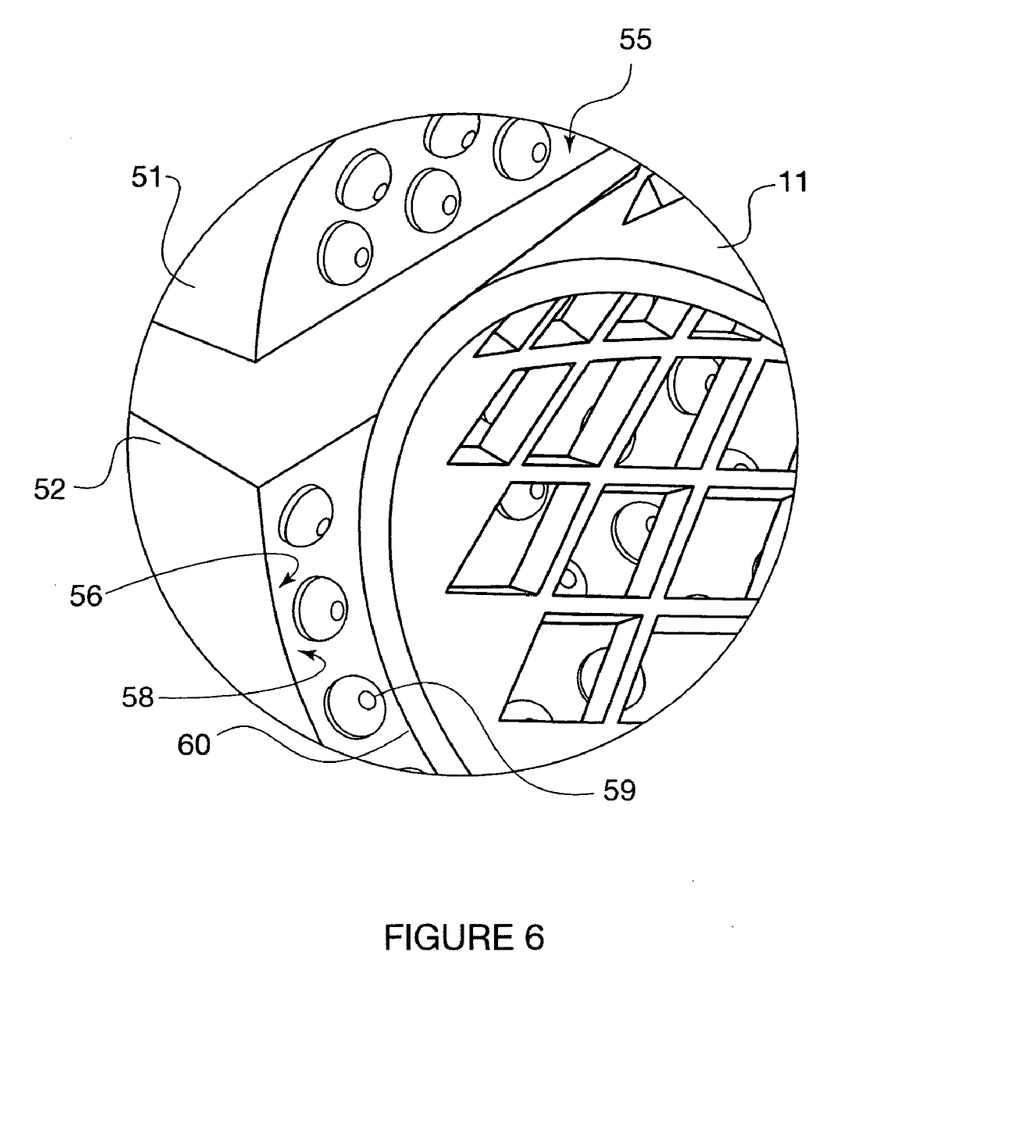
FIG. 6 illustrates a close-up view of the clamping device shown in FIG. 5 with a stent being clamped.

FIG. 6 illustrates a close-up view of clamping device 50 shown in FIG. 5 with stent 11 being clamped. Also shown are upper clamp section 51 and lower clamp section 52. Upper clamping surface 55 of upper clamp section 51 and lower clamping surface 56 of lower clamp section 52 are also shown in FIG. 6. Pattern region 58 is arranged on lower clamping surface 56, and a similar pattern is arranged on upper clamping surface 55. Pattern region 58 includes dimples 59 arranged in a uniform pattern. Stent 11 contacts lower clamping surface 56 at contact region 60.

Figure 7:
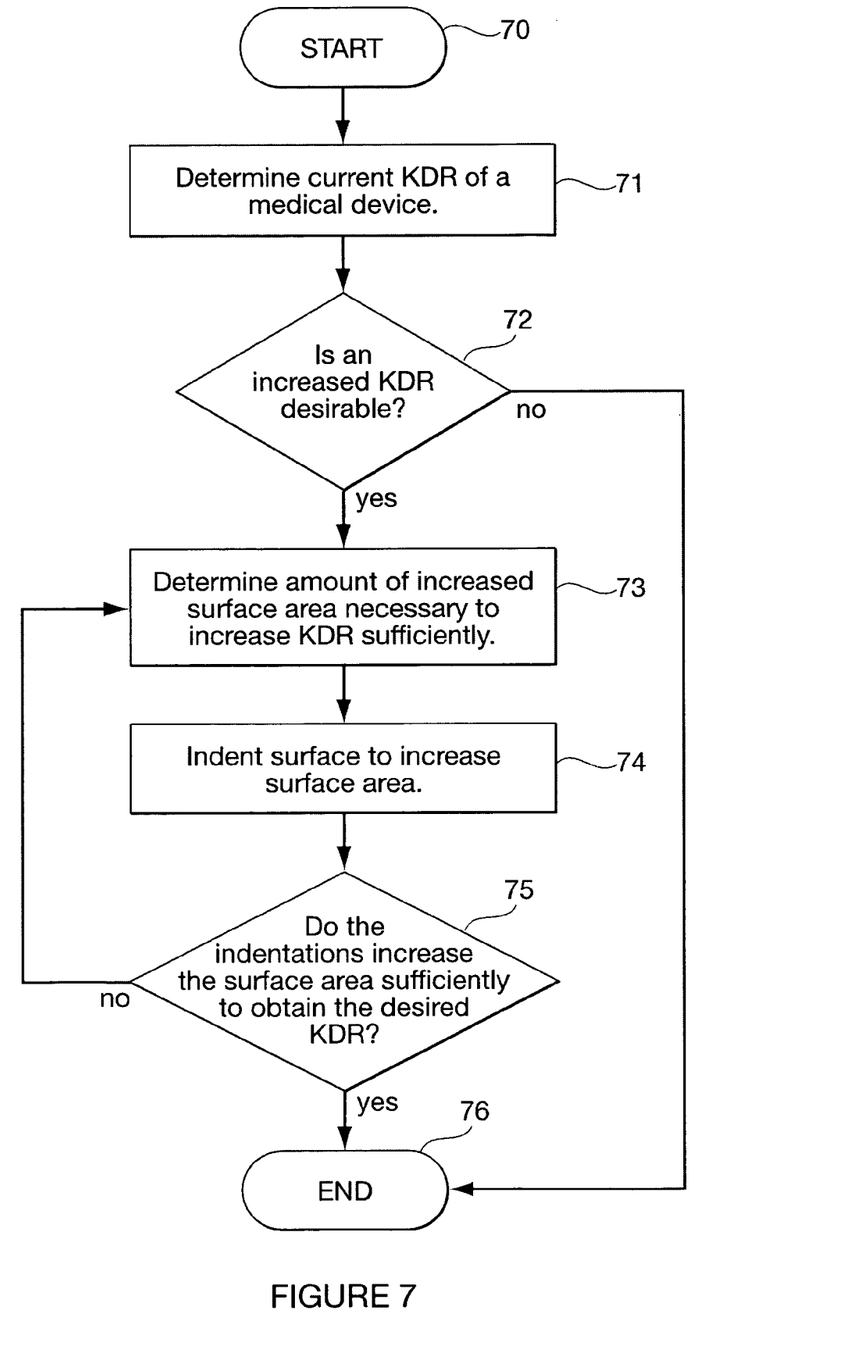
FIG. 7 illustrates a flowchart of an exemplary method of the present invention.

FIG. 7 illustrates a flowchart of an exemplary method of the present invention. The flow in FIG. 7 starts in start circle 70 and proceeds to action 71, which indicates to determine a current KDR of a medical device. From action 71, the flow proceeds to question 72, which asks whether an increased KDR is desirable. If the answer to question 72 is affirmative, the flow proceeds to action 73, which indicates to determine the amount of increased surface area necessary to increase the KDR sufficiently. From action 73, the flow proceeds to action 74, which indicates to indent the surface to increase the surface area. From action 74, the flow proceeds to question 75, which asks whether the indentations increased the surface area sufficiently to obtain the desired KDR. If the answer to question 75 is negative, the flow proceeds to action 73. If the answer to question 75 is affirmative, the flow proceeds to end circle 76. If the answer to question 72 is negative, the flow proceeds to end circle 76.

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof, antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α; hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyisobutylene copolymers and styrene-isobutylene-styrene block copolymers such as styrene-isobutylene-styrene tert-block copolymers (SIBS); polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A method for altering a drug release profile of a coating on a medical device, comprising:
   providing a medical device with a drug eluting coating on the medical device;
   providing a crimping apparatus adapted to indent the coating on the medical device; and
   using the crimping apparatus to indent the coating on the medical device, thereby increasing the surface area of the coating of the medical device to obtain an altered drug release profile.

2. The method of claim 1, wherein the indenting of the coating comprises creating at least one of angular indentations, rounded dimples, curved impressions, and linear edge impressions.

3. The method of claim 1, wherein the indenting of the coating comprises creating at least one of random indentations and regularly patterned indentations.

4. The method of claim 1, further comprising, prior to indenting the coating, the steps of:
   determining a surface area of the coating of the medical device; and
   determining an increased surface area necessary to alter the drug release profile to the altered drug release profile;
   wherein the step of indenting the coating increases the surface area of the coating to achieve the altered drug release profile.

5. The method of claim 1, wherein the crimping apparatus comprises a plurality of iris elements, each iris element adapted to indent the coating on the medical device.

6. The method of claim 1, wherein the medical device is a stent, and wherein the crimping apparatus is used to crimp the stent onto a balloon catheter.

7. A method for improving a drug release profile of a coating of a medical device, comprising:
   determining an expected drug release profile of the coating of the medical device using first process parameters of a coating method;
   determining an increased surface area necessary to obtain an improved drug release profile; and
   altering the first process parameters to second process parameters of the coating method to achieve the increased surface area;
   wherein the altering of the first process parameters to the second process parameters comprises changing a chemical composition of at least one coating component to increase a roughness of a texture of the coating.

8. A method for improving a drug release profile of a coating of a medical device, comprising:
   determining an expected drug release profile of the coating of the medical device using first process parameters of a coating method;
   determining an increased surface area necessary to obtain an improved drug release profile; and
   altering the first process parameters to second process parameters of the coating method to achieve the increased surface area;
   wherein the altering of the first process parameters to the second process parameters comprises one of drying and partially drying the coating before the coating strikes the medical device.

9. A method for altering a drug release profile of a coating on a medical device, comprising:
   providing a medical device with a drug eluting coating on the medical device;
   providing a rolling apparatus adapted to indent the coating on the medical device by causing the medical device to roll against at least one indenting surface; and
   using the rolling apparatus to indent the coating on the medical device, thereby increasing the surface area of the coating of the medical device to obtain an altered drug release profile.

10. The method of claim 9, wherein the indenting of the coating comprises creating at least one of angular indentations, rounded dimples, curved impressions, and linear edge impressions.

11. The method of claim 9, wherein the indenting of the coating comprises creating at least one of random indentations and regularly patterned indentations.

12. The method of claim 9, further comprising, prior to indenting the coating, the steps of:
    determining a surface area of the coating of the medical device; and
    determining an increased surface area necessary to alter the drug release profile to the altered drug release profile;
    wherein the step of indenting the coating increases the surface area of the coating to achieve the altered drug release profile.

13. The method of claim 9, wherein the rolling apparatus comprises at least one plate having at least one indenting surface adapted to indent the coating on the medical device.

14. The method of claim 13, wherein the medical device is rolled relative to the plate.

15. A method for altering a drug release profile of a coating on a medical device, comprising:
    providing a medical device with a drug eluting coating on the medical device;
    providing a clamping device adapted to indent the coating on the medical device; and
    using the clamping device to indent the coating on the medical device, thereby increasing the surface area of the coating of the medical device to obtain an altered drug release profile.

16. The method of claim 15, wherein the indenting of the coating comprises creating at least one of angular indentations, rounded dimples, curved impressions, and linear edge impressions.

17. The method of claim 15, wherein the indenting of the coating comprises creating at least one of random indentations and regularly patterned indentations.

18. The method of claim 15, further comprising, prior to indenting the coating, the steps of:
    determining a surface area of the coating of the medical device; and
    determining an increased surface area necessary to alter the drug release profile to the altered drug release profile;
    wherein the step of indenting the coating increases the surface area of the coating to achieve the altered drug release profile.

19. The method of claim 15, wherein the clamping device comprises an upper clamp section and a lower clamp section.

20. The method of claim 19, wherein the upper clamp section and the lower clamp section are connected by a hinge.

* * * * *